United States Patent [19]

Hardy et al.

[11] Patent Number: 4,681,592
[45] Date of Patent: Jul. 21, 1987

[54] PERACID AND BLEACH ACTIVATOR COMPOUNDS AND USE THEREOF IN CLEANING COMPOSITIONS

[75] Inventors: Frederick E. Hardy, Newcastle upon Tyne; Barry T. Ingram, Whitley Bay, both of England

[73] Assignee: The Procter & Gamble Company, Cincinnati, Ohio

[21] Appl. No.: 747,468

[22] Filed: Jun. 21, 1985

[30] Foreign Application Priority Data

Jun. 21, 1984 [GB] United Kingdom ............... 8415909

[51] Int. Cl.$^4$ ..................... D06L 3/06; C07C 69/00
[52] U.S. Cl. ............................ 8/111; 252/95; 252/99; 252/102; 252/547; 252/186.38; 560/129
[58] Field of Search ............. 252/186.38, 95; 8/111; 560/129

[56] References Cited

U.S. PATENT DOCUMENTS

| | | | |
|---|---|---|---|
| 2,955,905 | 10/1960 | Davies et al. | 252/103 |
| 3,272,750 | 9/1966 | Chase | 252/99 |
| 4,221,675 | 9/1980 | Schiermann et al. | 252/94 |
| 4,225,452 | 9/1980 | Leigh | 252/102 |
| 4,412,934 | 11/1983 | Chung et al. | 252/95 |
| 4,483,781 | 11/1984 | Hartman | 252/174.12 |

FOREIGN PATENT DOCUMENTS 3304848  8/1984  Fed. Rep. of Germany.
1382594  2/1975  United Kingdom.

OTHER PUBLICATIONS

Gilbert, A. H., "Effective Bleaching with Sodium Perborate", Detergent Age, Part I, Jun. 1967, pp. 18–20; Part II, Jul. 1967, pp. 30–33; and Part III, Aug. 1967, pp. 26–27, 67.

*Primary Examiner*—Paul Lieberman
*Assistant Examiner*—John F. McNally
*Attorney, Agent, or Firm*—Robert B. Aylor; Richard C. Witte; Thomas H. O'Flaherty

[57] ABSTRACT

Per-acids and per-acid precursor compounds of the general type RXAOOH and RXAL, wherein R is a hydrocarbyl group, X is a hetero-atom. A is a carbonyl bridging group and L is a leaving group, especially oxybenzenesulfonate, are useful bleaching compounds for fabrics. Laundry products containing same are disclosed.

22 Claims, No Drawings

PERACID AND BLEACH ACTIVATOR COMPOUNDS AND USE THEREOF IN CLEANING COMPOSITIONS

TECHNICAL FIELD

The present invention relates to novel peracids and means for preparing same, for example from various peracid precursor compounds. The peracids herein find use as laundry bleaches, and the peracid precursor compounds fall within the general class of laundry "bleach activator".

BACKGROUND

Peroxyacids (herein "peracids") are a well-known class of organic compounds that can be prepared, for example, by the action of hydrogen peroxide on organic acids in the presence of an acid catalyst. See ORGANIC PEROXIDES. E. G. E. Hawkins, D. Van Nostrand Company, Inc. (1961). Peracids have a variety of industrial uses, for example, as catalysts and as oxidizing agents.

Peracids also find use as cleaners and laundry bleaches. As such, the formulator typically prepares a relatively stable compound (a so-called "bleach activator") which decomposes in water in the presence of inorganic percarbonate or perborate to form the peracid in situ in a laundry liquor. See, generally, British No. 864 768; Canadian No. 635 620; U.S. Pat. Nos. 4,100,095; 4,119,660; 4,126,573; 4,412,934 and EPO published applications 0 068 547, 83 303 675.9. See especially U.K. No. 1 382 594 for Quat-Activators.

As can be seen from the extensive literature, there is a continuing search for new, more effective peracids and bleach activators. One major problem with some activators (or their degradation products, in-use) is poor odor quality. Another problem is that some activators are either rather complicated structures, or are made from rather expensive raw materials; in either event, many art-disclosed materials have remained laboratory curiosities rather than visible commercial items.

The present invention provides peracids and bleach activators which are readily prepared from inexpensive raw materials, and which do not suffer form the problems associated with many art-disclosed bleaching agents.

SUMMARY OF THE INVENTION

The present invention encompasses peracid compounds of the formula $[RX]_m AOOH$: where R is hydrocarbyl or alkoxylated hydrocarbyl, for example, $R(OCH_2CH_2)_y$—: X is a heteroatom-containing moiety, e.g., O, $SO_2$, $N(R')_2$, $P(R')_2$, $N(R') \rightarrow O$ or $P(R') \rightarrow O$, wherein R' is H or alkyl:
wherein for m=1, A is

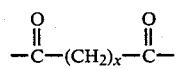

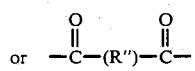

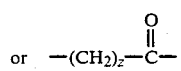

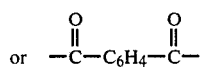

where x is an integer from 0 to 4, y is an integer of preferably 0 to 10 and z is an integer from 0 to 2, and R" is branched-chain alkylene, generally $C_3$–$C_{15}$; and wherein for m=2, A is

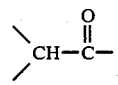

Preferred compounds herein are those wherein X is oxygen.

The invention also encompasses a method of cleaning fabrics or surfaces by contacting same with a peracid of the type disclosed herein.

The invention also encompasses bleach activators of the formula $[RX]_m AL$:

wherein R, m, X and A are as defined for the peracids, above, and "L" is a leaving group, as described more fully, hereinafter.

The invention also encompasses bleaching compositions comprising the bleach activator and a peroxide source such as a perborate, percarbonate, or peroxide compounds, as well as such compositions containing conventional detersive surfactants.

The invention also encompasses bleaching articles comprising the aforesaid bleach activators affixed to a substrate, preferably in sheet form. Such articles are conveniently used as laundry additives, or the like.

In general, 'R' in the above formulas can be $C_1$–$C_{20}$ hydrocarbyl (including alkyl, alkenyl, alkynyl, alk-aryl; branched or straight-chain or substituted) with $C_6$–$C_{20}$ alkyl or alkenyl or $C_6$–$C_{20}$ alkyl-substituted aryl being preferred. $C_6$–$C_{15}$ is especially preferred for oxidative stability. Also, the hydrocarbyl groups are optionally alkoxylated (i.e. linked to one or more ethyleneoxy or propyleneoxy groups or mixtures thereof).

DETAILED DESCRIPTION OF THE INVENTION

The compounds of this invention, and their synthesis, can best be understood by a consideration of the bleach activator compounds. It will be appreciated that the peracid compounds can be generated in situ from the activator compounds in aqueous media, in the presence of peroxide.

The bleach activator compounds can be described as comprising three parts: (i) an optionally alkoxylated hydrocarbyl part (designated 'R' in the general formula) said hydrocarbyl part being linked via a heteroatom ('X' in the formula) to (ii) a bridging part ('A' in the formula) which contains a labile carbonyl group; said bridging part being attached to a leaving group ('L' in the formula) at the labile carbonyl group; as follows:

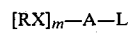

In use, the activator forms the active, bleaching peracids, as follows:

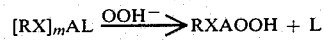

SYNTHESIS SCHEMES

The synthesis of the herein-disclosed peroxy acids per se employs standard chemical reactions, and such synthesis schemes form no part of the present invention. For example, the parent organic acid can be reacted with $H_2O_2$ in the presence of an inorganic acid catalyst to form an equilibrium aqueous mixture containing the organic peracid. Alternatively, the acid chloride or acid anhydride can be used with $H_2O_2$. Cationic ion-exchange resins may be used as the catalyst. Water-free peracids can be prepared by azeotropic distillation from alkyl acetate solvents. Dipicolinic acid can be used to reduce the danger of explosions when the pure acid is being isolated.

It is to be understood that there is no need to isolate the pure peracid in order to use it as a bleaching or cleaning agent; indeed, to do so is generally wasteful, since the peracid is typically used in solution rather than as the pure compound.

The peracids herein are most conveniently provided in situ when their respective bleach activator molecules are placed in the presence of a peroxide source (e.g. $H_2O_2$, sodium perborate or sodium percarbonate) and water at alkaline pH.

Having earlier considered the bleach activator molecules as comprising three parts, it becomes relatively simple to devise synthesis schemes for the various compounds herein, using well-known starting materials and chemical reactions.

For example, portion "RX" of the activators (and the peracids) can comprise the commercially-available alcohols (ROH) and amines ($RNH_2$). It will be appreciated that the N(H) hetero-atom will be more-or-less labile to self-oxidation unless limited to a carbonyl, i.e., amides. Hence in other cases substituent groups should preferably be alkyl (conveniently $C_1$–Chd 4) rather than hydrogen and are designated R' in the general formula, shown above.

The bridging group "A" of the activators (and the peracids) can comprise moieties derived from such commonly-available materials as oxalic acids (—C(O)—C(O)—); maleic acid (—C(O)CH=CHC(O)); phthalic acid (—C(O)$C_6H_4$C(O)—); adipic acid (—C(O)(CH$_2$)$_4$C(O)—); and the like. Such bridging moieties are all derivable by chemical reactions well known in the art The combination of "RXA" forms the parent acids from which the peracids can ben generated, as noted above, and also constitutes the parent acid of the bleach activators, which are formed from RXA acids and leaving groups "L".

With regard to leaving group "L", it will be appreciated from even a cursory review of the cited patent literature that there is a wide choice of chemical moieties which act as leaving groups and from which bleach activator molecules can be synthesized which are sufficiently stable for incorporation into a home laundry detergent, laundry bleach, or the like. Included among such known groups "L" are, for example: diacetyl ethylene diamine, which affords for example the commercially-important "Tetraacetyl Ethylenediamine; TAED" bleach activator; acetylated glycouril, which affords for example the tetraacetylglycouril "TAGU" bleach activator; acetylated glucose. which affords for example the pentaacetylglucose "PAG" bleach activators, and the like. Another important "L" group is the oxybenzenesulfonate group, which is particularly preferred for use in the practice of the present invention to form "OBS"-type bleach activators.

Although "L" groups are chemically diverse, they share the common property of splitting-off from the other ("RXA") portion of the activator molecule, for example, in the presence of water and an peroxide source such as $H_2O_2$ or an inorganic per-salt such as percarbonate or perborate, whereupon said other portion of the molecule (RXA) forms the peracid bleaching species.

Typical syntheses of compounds of the present will be given hereinafter, by way of illustration. However, since the bridging groups "A" of the parent RXA compounds contain active carbonyl substituents, thereby making them labile, alternative syntheses will be apparent to one skilled in the art.

INDUSTRIAL APPLICATIONS

The compounds of this invention can be used to clean and bleach fabrics in standard cleaning and laundering operations. One of the advantages of the bleach activator compounds disclosed herein is their stability in the presence of conventional cleaning and laundering agents. Accordingly, these compounds can be used in fully-formulated bleaching, cleaning and laundry compositions in combination with conventional detersive surfactants, detersive adjuncts, aesthetic materials such as perfumes or colorants, and the like. The following ingredients are mentioned by way of exemplification, but are not intended to be limiting.

Detersive Surfactants—The laundry and hard surface cleaning compositions of this invention will typically contain organic surface-active agents ("surfactants") to provide the usual cleaning benefits associated with the use of such materials.

Detersive surfactants useful herein include well-known synthetic anionic, nonionic, amphoteric and zwitterionic surfactants. Typical of these are the alkyl benzene sulfonates, alkyl- and alkylether sulfates, paraffin sulfonates, olefin sulfonates, alkoxylated (especially ethoxylated) alcohols and alkyl phenols, amine oxides, α-sulfonates of fatty acids and of fatty acid esters, and the like, which are well-known from the detergency art. In general, such detersive surfactants contain an alkyl group in the $C_9$–$C_{18}$ range; the anionic detersive surfactants can be used in the form of their sodium, potassium or triethanolammonium salts; the nonionics generally contain from about 5 to about 17 ethylene oxide groups. U.S. Pat. Nos. 4,111,855 and 3,995,669 contain detailed listings of such typical detersive surfactants. $C_{11}$–$C_{16}$ alkyl benzene sulfonates, $C_{12}$–$C_{18}$ paraffin-sulfonates and alkyl sulfates, and the ethoxylated alcohols and alkyl phenols are especially preferred in the compositions of the present type.

Also useful herein as the surfactant are the water-soluble soaps, e.g. the common sodium and potassium coconut or tallow soaps well-known in the art.

The surfactant component can comprise as little as 1% of the compositions herein, but preferably the compositions will contain 1% to 40%, preferably 10% to 40%, of surfactant. Mixtures of the ethoxylated nonionics with anionics such as the alkyl benzene sulfonates, alkyl sulfates and paraffin sulfonates are preferred for through-the-wash cleansing of a broad spectrum of soils and stains from fabrics.

Detersive Adjuncts—The compositions herein can contain other ingredients which aid in their cleaning performance. For example, it is highly preferred that fully-formulated detergent compositions contain a detergent builder and/or metal ion sequestrant. Compounds classifiable and well-known in the art as detergent builders include the nitrilotriacetes, polycarboxylates, citrates, water-soluble phosphates such as tripolyphosphate and sodium ortho- and pyro-phosphates, silicates, and mixtures thereof. Metal ion sequestrants include all of the above, plus materials like ethylenediaminetetraacetate, the amino-polyphosphonates and phosphates (DEQUEST) and a wide variety of other poly-functional organic acids and salts too numerous to mention in detail here. See U.S. Pat. No. 3,579,454 for typical examples of the use of such materials in various cleaning compositions. In general, the builder/sequestrant will comprise about 0.5% to 45% of the composition. The 1–10 microns size zeolite (e.g. zeolite A) builders disclosed in German Pat. No. 2,422,655 are especially preferred for use in low-phosphate compositions which contain the bleach activators described herein.

The laundry compositions herein also preferably contain enzymes to enhance their through-the-wash cleaning performance on a variety of soils and stains. Amylase and protease enzymes suitable for use in detergents are well-known in the art and in commercially available liquid and granular detergents. Commercial detersive enzymes (preferably a mixture of amylase and protease) are typically used at levels of 0.001% to 2%, and higher, in the present compositions.

Moreover, the compositions herein can contain, in addition to ingredients already mentioned, various other optional ingredients typically used in commercial products to provide aesthetic or additional product performance benefits. Typical ingredients include pH regulants, perfumes, dyes, optical brighteners, soil suspending agents, hydrotropes and gel-control agents, freeze-thaw stabilizers, bactericides, preservatives, suds control agents, and the like. Such ingredients typically comprise 0.5% to 15% of laundry detergents.

Laundry detergent or bleaching/cleansing compositions comprising the herein-disclosed bleach activators will also contain a source of hydrogen peroxide. Sodium perborate is typically used, but other per-salts such as sodium percarbonate or various hydrogen peroxide "adducts" such as urea-peroxide may be chosen, according to the desires of the formulator. Such peroxy-source compounds will typically comprise 5%–30% of a fully-formulated laundry compositions, and 5% to 99.5% of a simple bleach composition.

In a through-the-wash laundry mode, the compositions are typically used at a concentration of at least 500 ppm, preferably 0.10% to 2.5%, in an aqueous laundry bath at pH 7-11 to launder fabrics. The laundering can be carried out over the range from 5° C. to the boil, with excellent results.

In an alternate mode, the bleach activators herein may be releasably adsorbed or releasably coated onto a substrate such as a non-woven or paper sheet or flexible sponge mat, or the like. Such objects (preferably, in sheet-form) may be added to the laundry or cleaning bath where the activator is released to combine with a peroxide source to enhance bleaching action.

Such sheet-form products will generally employ 1–20 grams the bleach activator per sheet.

The following are typical examples of bleaching and laundry compositions and processes of the present invention, but are given only by way of illustration and are not intended to be limiting of the scope of the invention. All percentages and ratios mentioned in this specification are by weight, unless otherwise indicated.

The preferred laundry compositions generally contain 1% to 25% of the activator.

EXAMPLE I

A laundry additive in sheet-form is prepared using a piece of flexible, non-woven cloth 20 cm×20 cm. 3.5 grams of the bleach activator of Example A (hereinafter) are admixed with 5 grams of a 80:20 melt of ditallow dimethyl ammonium chloride and monotallow trimethyl ammonium bromide. The resulting mixture is paddee evenly onto the surfaces of the sheet and allowed to solidify. In-use, the sheet is added to a conventional, aqueous laundry liquor containing a conventional perborate detergent. The activator is released from the sheet to provide enhanced bleaching performance throughout the wash cycle.

EXAMPLE II

A bleach composition in granular form is prepared as follows.

| Ingredient | Percent |
|---|---|
| Sodium Perborate ($4H_2O$) | 90 |
| Bleach Activator* | 10 |

*Prepared in Example B (hereinafter).

The composition of Example II is prepared by simply dry-blending the perborate granules (0.3–6 mm) with the bleach activator. In a preferred mode, the bleach activator is coated with tallow ethoxylate (11) and formed into agglomerates (0.3–6 mm) in a pan agglomerator. This treatment provides two benefits. First, by equalizing the particle sizes of the perborate and activator, the final product retains its homogeneity after dry-blending. Second, the TAE(11) protects the activator from prematurely realting with the perborate.

In-use, the composition of Example II is added to water to form a bleaching/cleaning solution suitable for use on hard surfaces or fabrics. Of course, the amount used will depend on the difficulty of the particular cleaning chore, but, in general, quantities of 10–50 grams per 10 liters of water are used.

The composition of Example II can be modified by replacing the sodium perborate with sodium percarbonate. When so doing, it is preferred to coat both the percarbonate and the bleach activator with TAE(11) to provide additional stability of the product on long-term storage, especially under humid conditions.

EXAMPLE III

A fully-formulated granular laundry detergent is as follows. The percentages are by weight of the final formula.

| Ingredient | Percent |
|---|---|
| (a) Sodium toluene sulfonate | 0.7 |
| (a) Sodium linear $C_{12}$ alkyl benzene sulfonate | 7.5 |
| (a) Sodium tripolyphosphate | 30.0 |

| Ingredient | Percent |
| --- | --- |
| (a) Sodium Silicate (SiO$_2$:Na$_2$O ratio 1.6:1) | 5.5 |
| (b) Sodium Perborate tetrahydrate | 24.0 |
| (a) Sodium sulphate | 15.0 |
| (a) Tallow ethoxylate (EO 9–11) | 4.0 |
| (a) Optical brightener | 0.2 |
| (b) Proteolytic Enzyme | 0.3 |
| (b) Bleach Activator* | 3.5 |
| (a) Moisture and miscellaneous | balance |

*prepared in Example C (hereinafter)

The composition of Example II is made by first forming designated ingredients (a) into standard spray dried base granules via an aqueous crutcher mix. The remaining ingredients (b) are then dry-mixed with the base granules.

EXAMPLE IV

A spray-dried detergent formulation with zeolite builder is as follows:

| Ingredient | Percent |
| --- | --- |
| Zeolite A (1–10 micron) | 25.0 |
| Sodium nitriotriacetate | 5.0 |
| C$_{11-12}$ alkyl benzene sulfonate (Na) | 6.5 |
| Tallow ethoxylate (EO 9–11) | 1.0 |
| Sodium perborate.4H$_2$O* | 20.0 |
| Sodium silicate | 8.0 |
| CMC | 1.0 |
| Sodium sulfate | 20.0 |
| Enzymes (1:1 amylase/protease)* | 1.5 |
| Optical brightener | 0.5 |
| Sodium toluene sulfonate | 1.0 |
| Bleach Activator** | 5.0 |
| Water, minors, perfume* | to 100 |

*Ingredients added to base granule after spray-drying
**Bleach activator prepared in Example B (hereinafter) and added to the base granule after spray-drying.

The following Examples A–C illustrate the synthesis of the more highly preferred bleach activator compounds of this invention. Highly-branched compounds of the formula [RO]$_2$CHC(O)OOH and RO$_2$CHC(O)L can be prepared from the corresponding branched acids of the formula [RO]$_2$CHCOOH, available by the reaction sequence disclosed in U.S. Pat. No. 4,419,258 (Crutchfield; assigned Monsanto Co.). As mentioned hereinabove, the other alcohol, thiol, amine and phosphine reactants are well-known in the literature.

The preferred compounds herein have group "L" as oxybenzenesulfonate. It is convenient to introduce this group onto the parent acids (via their respective acid chlorides) using disodium p-phenolsulfonate in, for example, dry diglyme solvent. A convenient preparation of the phnolsulfonate is as follows:

PREPARATION OF DISODIUM P-PHENOSULFONATE

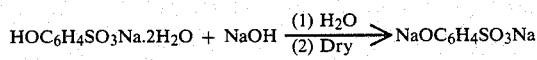

Disodium p-phenolsulfonate is prepared by adding a solution of 483.5 g (12.1 moles) of sodium hydroxide in 750 ml of water to 2784 g (12.0 mole) of the monosodium salt dihydrate dispersed in 2 l. of water. The final pH of this mixture is 10.6. Most of the water is evaporated in a rotary evaporator and the resulting rigid solid is transferred to a vacuum oven for final drying at 115°–120° C.

EXAMPLE A

C$_{14-15}$ (E7)-oxycarbonyloxybenzenesulfonic ("OCOBS") acid or salt

A commercially-available C$_{14-15}$ chain-length alcohol ethoxylated with an average of 7 moles ethylene oxide (as DOBANOL ® 45-E7) (105.3 g; 0.2 mole) was dissolved in toluene (250 ml) and, using a Dean-Stark trap, toluene (50 ml) was distilled out to remove traces of water. The solution was cooled to 0°–5° C. in a flask fitted with reflux condenser, drying-tube and gas-inlet port. A 12% solution of phosgene in toluene (220 g) was slowly added with vigorous stirring. The mixture was stirred at 0°–5° C. for 30 min, then allowed to warm to room temperature and stirred for 2 hrs. more. The product was purged with nitrogen to remove HCl and excess phosgene and then solvent was removed on a Rotavapor. Yield 121.6 g.

The disodium salt of p-phenolsulfonate (35 g) was added to diglyme (bis-2-methoxyethyl ether: 500 ml) and diglyme (50 ml) was distilled out to remove traces of water. The resulting suspension was cooled to 100° C. and the Dobanol 45 E7.chloroformate, prepared above, was slowly added with vigorous stirring and these reaction conditions were maintained for 1 hr. On cooling the mixture was poured into vigorously agitated diethyl ether and filtered. The crude product was twice redispersed in ether and refiltered. Yield on drying was 75.1 g. Purity by Cat SO$_3$ titration was 82.1% (most of the impurity was by-product salt).

Dobanol 91-E5 and Coconut-E1 ethoxylates were converted to OCOBS in like manner.

EXAMPLE B

2-Ethylhexanol (50 g; 0.38 mole) and succinic anhydride (38 g; 0.38 mole) were heated and stirred at 120° C. until the mixture clarified and then at 100° C. for 30 min. Thionyl chloride (55 min; 0.76 mole) was added after cooling and the mixture was stirred at 35° C. for 3 hr. Excess thionyl chloride was removed on a Rotavapor.

Disodium p-phenolsulfonate (63.7 g; 0.29 mole) was suspended in digylme (600 ml) and solvent (20 ml) was distilled out to remove traces of water. The stirred mixture was cooled to 95° C. and 2-ethylhexylsuccinyl chloride prepared above was added dropwise over 15 min. Stirring was continued for 30 min at 100° C. and the suspension was cooled and poured into vigorously agitated diethyl ether. The crude product (2-ethylhexylsuccinyl oxybenzenesulfonate) was filtered off, suspended twice in more ther, with refiltration, and dried. Yield was 100 g and purity was 76% by Cat SO$_3$ titration (major impurity was NaCl).

EXAMPLE C

Octylsuccinic anhydride (56 g; 0.27 mole) and excess isopropanol were boiled under reflux for 1.5 hr and unreacted solvent was removed on a Rotavapor. Thionyl chloride (38 ml; 0.53 mole) was added and the solution was stirred at 35° C. for 3 hr. Volatiles and excess reagent were again removed by rotary evaporation.

Disodium phenolsulfonate (47 g; 0.22 mole) was suspended in diglyme (150 ml) and solvent (10 ml) was distilled out to dry the system. Isopropyl-octylsuccinyl chloride was added dropwise over 15 min to the suspension stirred at 100° C. Stirring was continued for 30 min at 100° C. The cooled mixture was poured into stirred ether and the crude product (isopropyl-octylsuccinyl oxybenzenesulfonate) was filtered, twice rewashed and refiltered with ether and dried. Yield was 47.5 g and purity (CatSO$_3$) was 70.5%. (Major impurity was NaCl).

Having thus illustrated the present invention with regard to chemical syntheses and cleaning compositions, it is readily seen by one skilled in the art that the compounds herein may be considered to be derivatives of known acids (as group A'), as follows (shown with "L" as oxybenzenesulfonate (OBS) and "X" as oxygen).

| A' | | ACOOH | ROAL |
|---|---|---|---|
| 1. | HO— | Carbonic acid | RO.CO.OC$_6$H$_4$SO$_3$Na |
| 2. | HOCH$_2$= | Glycollic acid | ROCH$_2$CO.OC$_6$H$_4$SO$_3$Na |
| 3. | CH$_2$=CH— | Acrylic acid | ROCH$_2$CH$_2$CO.O.C$_6$H$_4$SO$_3$Na |
| 4. | HO—OC— | Oxalic acid | RO.OC.CO.OC$_6$H$_4$SO$_3$Na |
| 5. | OCH— | Glyoxylic Acid | [RO]$_2$CH$_2$COOC$_6$H$_4$SO$_3$Na |
| 6. | HO.OC—CH$_2$CH$_2$= | Succinic acid | ROOC[CH$_2$]$_2$COOC$_6$H$_4$SO$_3$Na |
| 7. | HOOCCH=CH— | Maleic, fumaric acids | ROOCCH=CH—COOC$_6$H$_4$SO$_3$Na |

In general, the presence of the heteroatom (X) in the molecule enhances the acidity of A'COOH, and this will be reflected in lower nucleophilicity of the corresponding peranion and hence less diacyl peroxide formation and higher peracid yield.

Although the compounds herein have been illustrated in the form of their OBS derivatives, the synthesis of compounds with different leaving groups "L" is easily achieved by known reactions. Generally, for a group to the a suitable leaving group it must exert an electron withdrawing effect within the precursor molecule, as this facilitates the nucleophilic displacement by the perhydroxide anion.

Suitable leaving groups for this purpose have conjugate acid forms, the pKa of which should lie within the range from 6 to 13. pKa values above 13 make the electron withdrawal effect so small as to be ineffective in promoting nucleophilic attack by perhydroxide anion, an example of such a leaving group being —OCH$_3$. pKa values below 6 reflect such a large electron withdrawal effect as to make the molecule reactive to a wide variety of materials including e.g. water. Certain aliphatic ahydrides fall into this class. Preferred leaving groups have a pKa in the range from 7 to 11, more preferably from 8 to 10.

However for the purposes of the present invention the leaving group should preferably confer a degree of solubility on the precursor molecule so that it partitions between the aqueous phase and any organic phase present in a laundry liquor, for example. Certain leaving groups such as sulphonamide(s) groups, having conjugate acid forms of the appropriate pKa, do not provide sufficient aqueous solubility to the precursor molecule and therefore do not give a sufficient rate of perhydrolysis to be practicable in a laundry detergent liquor.

In summary, leaving groups "L" to be especially useful in laundry bleach compounds of the present invention are those having the formula

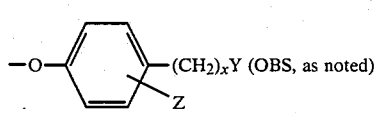 (CH$_2$)$_x$Y (OBS, as noted) (a)

and

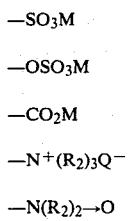 (b)

wherein Z is H, R$_2$ or halide; R$_2$ is an alkyl group containing from 1 to 4 carbon atoms; x is 0 or an integer from 1 to 4 and Y is selected from:

—SO$_3$M

—OSO$_3$M

—CO$_2$M

—N$^+$(R$_2$)$_3$Q$^-$

—N(R$_2$)$_2$→O wherein M is H, alkali metal, alkali earth metal ammonium or substituted ammonium, and Q is halide or methosulphate.

The preferred leaving group L has the formula (a) in which Z is H, x is 0, and Y is a sulfonate, carboxylate or dimethyl amine oxide radical.

The position of the solubilising group Y on the benzene ring in formula (a) is not critical in that o-, m- and p-positions provide operable species. Nevertheless polar and steric factors make the o-substituted material most difficult to synthesise and of least value in that steric hindrance impedes the approach of perhydroxyl ion.

In the preferred embodiment of leaving group L, where Y is a sulfonate radical, the precursor will normally be isolated in the form of its alkali metal salt because of the difficulty of handling the acid form.

In summary, the compounds herein provide several advantages over perbleaches and bleach activators known from the art. Firstly, the presence of the heteroatom decreases their vapor pressure, thereby reducing malodors. Secondly, having performed their bleaching function, selected compounds from the class decompose in laundry liquors to provide additional cleaning benefits. For example, compounds containing an ethoxylated hydrocarbyl group, especially C$_{10}$-C$_{18}$ alkyl or alkylphenyl with above about 3 EO units, especially 5-15 EO units, yield nonionic (EO) surfactants or ethoxy soaps as their decomposition products, and these, of course, can contribute to fabric cleaning in a laundry bath. Other compounds herein decompose to yield fabric-substantive fabric softeners.

It will be appreciated that the presence of heteroatomsin the molecule enhances the acidity of the parent acid of the per-acid compounds. This enhanced acidity will be reflected in lower nucleophilicity of the corresponding peranion which, as noted above, yields more of the desired peracid and less diacyl peroxide formation.

The acidity can be described by the equation $$pKa = 4.66 - 1.62\sigma^*$$

where $\sigma^*$ is the TAFT value of the heteroatom containing group. (On the Taft Scale, $\sigma^*$ for CH$_3$— i.e., acetic acid—is zero. Accordingly, hetero substituents with $\sigma^*$ of positive value decrease pKa and lead to the desirable advantages noted above. See "pKa Prediction for Organic Acids and Bases" by Perrin, Dempsey and Serveant; Chapman and Hall (1981).

Likewise, electron-withdrawing groups present in the hydrocarbyl side-chains of the compounds herein both lower vapor pressures and enhance per-acid formation and, consequently, enhance bleaching performance. Included among such groups are, for example, chloro-, bromo-, methoxy-, ethoxy-, trifluoromethyl-, and the like. Such electron-withdrawing groups are well-known to the organic chemist, and are described by the Perrin text, as noted above. The present invention employs the term "Hydrocarbyl" as including such groups on the hydrocarbyl chain, preferably at the carbon atom adjacent, or next adjacent, the heteroatom.

What is claimed is:

1. Peracids of the formula:

wherein

R is hydrocarbyl, selected from the group consisting of optionally substituted, linear and branched C$_6$-C$_{20}$ alkyl and alkenyl and C$_6$-C$_{20}$ alkyl-substituted aryl; or alkoxylated hydrocarbyl;

X is selected from the group consisting of O, SO$_2$, N(R')$_2$, P(R')$_2$, (R')P→O and (R')N→O; m is either 1 or 2; and wherein for m=1, A is selected from the group consisting of

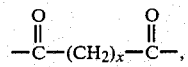

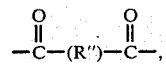

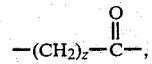

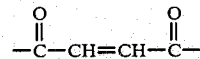

and

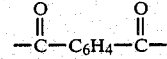

where x is an integer from 0 to 4; z is an integer from 0 to 2; (R') is alkyl and R" is branched-chained alkylene and wherein for m=2, A is

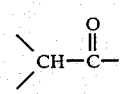

2. A peracid according to claim 1 wherein X is oxygen.

3. A peracid according to claim 2 wherein R is optionally alkoxylated C$_{6-15}$ alkyl.

4. A peracid according to claim 3 of the formula ROC(O)CH$_2$CH$_2$C(O)OOH.

5. A peracid according to claim 4 wherein R is C$_6$-C$_{10}$ alkyl.

6. A peracid according to claim 3 of the formula RO(CH$_2$CH$_2$O)$_y$C(O)OOH wherein y is an integer from 0 to 10.

7. A peracid according to claim 6 wherein R is C$_{14}$-C$_{15}$ alkyl and y is an integer from 1-7.

8. A peracid according to claim 3 of the formula ROC(O)C(O)OOH.

9. A peracid according to claim 8 wherein R is C$_6$-C$_{10}$ alkyl.

10. A peracid according to claim 3 of the formula (RO)$_2$CHC(O)OOH.

11. A peracid according to claim 10 wherein each R is C$_6$-C$_{10}$ alkyl.

12. A method of cleaning fabrics or surfaces comprising contacting said fabrics or surfaces with a peracid according to claim 1.

13. A bleach activator compound of the formula

wherein R is hydrocarbyl, selected from the group consisting of optionally substituted, linear and branched C$_6$-C$_{20}$ alkyl and alkenyl and C$_6$-C$_{20}$ alkyl-substituted aryl; or alkoxylated hydrocarbyl; X is selected from the group consisting of O, SO$_2$, N(R')$_2$, P(R')$_2$, (R')P→O and (R')N→O; m is either 1 or 2; and wherein for m=1, A is selected from the group consisting of

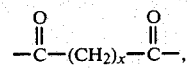

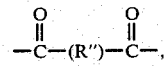

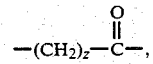

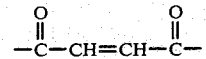

and

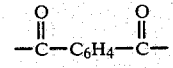

where x is an integer from 0 to 4; z is an integer from 0 to 2; (R') is alkyl and R" is branched-chain alkylene and wherein for m=2, A is

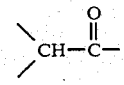

and wherein L is a leaving group selected from the group consisting of:

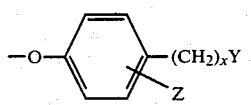

and

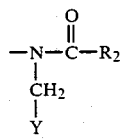

wherein
x is an integer from 0 to 8,
Z is H, $R_2$ or halide,
$R_2$ is $C_1$-$C_4$ alkyl, and
Y is selected from
—$SO_3M$
—$OSO_3M$
—$CO_2M$
—$N^+(R_2)_3Q^-$
—$N(R_2)_2\rightarrow O$
wherein M is H, alkali metal, alkaline earth metal, ammonium or substituted ammonium and Q is halide or methosulphate.

14. A bleach activator compound according to claim 13 wherein X is oxygen and the leaving group 'L' is (a) 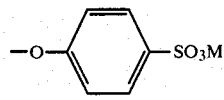

(b)

15. A bleach activator compound according to claim 14 which is $C_{14\text{-}15}$ (Ethoxy-7)-oxycarbonyloxybenzenesulfonic acid or salt thereof.

16. A bleach activator compound according to claim 14 which is 2-ethylhexylsuccinyl oxybenzenesulfonic acid or salt thereof.

17. A bleach activator compound according to claim 14 which is isopropyl-octylsuccinyl oxybenzenesulfonic acid or salt thereof.

18. A cleaning composition comprising a mixture of a bleach activator compound according to claim 13 and a perborate, percarbonate or peroxide compound.

19. A composition according to claim 18 which additionally comprises a detersive surfactant and which optionally comprises conventional detersive adjuncts.

20. A bleaching article comprising a bleach activator according to claim 13 affixed to a substrate preferably in sheet form.

21. A bleach activator compound according to claim 13 wherein group RX has a positive TAFT $\sigma^*$ value and wherein L is a water-soluble leaving group.

22. A cleaning composition containing a compound according to claim 21 and a peroxide source.

* * * * *